United States Patent
Wei et al.

(10) Patent No.: US 10,787,416 B1
(45) Date of Patent: Sep. 29, 2020

(54) CRYSTALS OF INTERMEDIATE FOR BENZINDENE PROSTAGLANDINS AND METHODS FOR PREPARATION THEREOF

(71) Applicant: CHIROGATE INTERNATIONAL INC., Yangmei (TW)

(72) Inventors: Shih-Yi Wei, Yangmei (TW);
Jian-Bang Jheng, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 0 days.

(21) Appl. No.: 16/868,624

(22) Filed: May 7, 2020

(51) Int. Cl.
*C07C 255/37* (2006.01)

(52) U.S. Cl.
CPC ........ *C07C 255/37* (2013.01); *C07B 2200/13* (2013.01)

(58) Field of Classification Search
CPC .......................... C07C 255/37; C07B 2200/13
USPC ....................................................... 558/389
See application file for complete search history.

(56) References Cited

U.S. PATENT DOCUMENTS 8,658,837 B2 * 2/2014 Wei .................. C07C 41/26
568/733

OTHER PUBLICATIONS

Byrn et al., Solid-State Chemistry of Drugs, 1999, SSCI, Inc., Second Edition, pp. 62-63 (Year: 1999).*
Chawla et al., Challenges in Polymorphism of Pharmaceuticals, CRIPS, vol. 5, No. 1, Jan.-Mar. 2004, pp. 9-12 (Year: 2004).*
Brittain etal., Polymorphism in Pharmaceutical Solids, 1995, vol. 95, p. 228-229 (Year: 1995).*
Vippagunta et al., Advanced Drug Reviews, 48 (2001), pp. 3-26 (Year: 2001).*

* cited by examiner

*Primary Examiner* — Kristin A Vajda
(74) *Attorney, Agent, or Firm* — Ladas & Parry LLP (57) ABSTRACT

Stable crystalline Form I and Form II of compound (I) and methods for preparation thereof are provided, which present advantages in storage, formulation, shipment and handling for commercial considerations.

14 Claims, 3 Drawing Sheets

CRYSTALS OF INTERMEDIATE FOR BENZINDENE PROSTAGLANDINS AND METHODS FOR PREPARATION THEREOF

FIELD OF THE INVENTION

The present invention relates in general to solid forms of an intermediate for benzindene prostaglandins, and in particular, to crystalline forms of 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetonitrile and preparation methods thereof.

BACKGROUND OF THE INVENTION 2-(((1R,2R,3aS,9aS)-2-hydroxy-1-((S)-3-hydroxyoctyl)-2,3,3a,4,9,9a-hexahydro-1H-cyclopenta[b]naphthalen-5-yl)oxy)acetonitrile (hereinafter referred to as compound (I)), as shown in the following Scheme A, is an important key intermediate for the synthesis of benzindene prostaglandins such as treprostinil, treprostinil sodium, treprostinil diethanolamine, hexadecyl treprostinil, and related derivatives.

Scheme A (I)

The synthesis processes of compound (I) have been disclosed by CN 103880801, US 2013/53581, U.S. Pat. No. 8,497,393, *J. Org. Chem.*, 2004, 69, 1890-1902, etc. However, according to the prior documents, only a viscous liquid of compound (I) is obtained during production. It is well known that a viscous liquid is an amorphous form of organic compound. Compared to a crystalline compound, the thermal stability, purity and homogeneity of an amorphous compound are not satisfactory. Moreover, an amorphous compound presents difficulties for commercial handling to avoid loss from sticking to the container due to its high viscosity.

Consequently, there is an urgent demand for the preparation of a stable crystalline form of compound (I) for use as an intermediate for the synthesis of benzindene prostaglandins.

SUMMARY OF THE INVENTION

Upon research, the inventor found a crystallization method for preparing crystalline forms of compound (I). The obtained stable crystalline forms of compound (I) with higher purity compared to amorphous ones can provide constant operating parameters, e.g., solubility for regular synthesis processes. Additionally, the stable crystalline forms of compound (I) can also present advantages in storage, formulation, handling and shipment and for commercially considerations.

In one aspect, the present invention provides crystals of compound (I), and processes for the preparation thereof (I)

Based on the above background, the inventor of the present invention conducted a series of research, and surprisingly found that the novel crystalline forms of compound (I) can be obtained by using ether solvents. On the other hand, it is very difficult to obtain a crystal of compound (I) using common solvents for commercial applications such as methyl isobutyl ketone, ethyl acetate, isopropyl acetate, toluene, xylene, acetone, dichloromethane, 1,4-dioxane, tetrahydrofuran, methanol, ethanol, propanol, butanol, benzyl alcohol, dimethyl sulfoxide, dimethylacetamide, dimethylformamide, and mixtures thereof. The present invention relates, at least in part, to two crystalline forms of compound (I). One of the crystalline forms is precipitated from ethyl ether, isopropyl ether, or methyl tert-butyl ether solution and termed crystalline Form I of compound (I). When methyl tert-butyl ether is used for preparing Form I, the volume is preferably less than about 20 ml per 1 g of the crude compound (I). The other crystalline form is precipitated from methyl tert-butyl ether solution only and termed crystalline Form II of compound (I), and the volume of methyl tert-butyl ether is preferably about 20 ml or more per 1 g of the crude compound (I).

In one embodiment, the present invention provides a crystalline Form I of compound (I) having an X-ray powder diffraction (XRPD) pattern exhibiting its six strongest characteristic peaks at the following 2θ reflection angles: 4.5±0.2°, 8.3±0.2°, 11.6±0.2°, 18.1±0.2°, 20.0±0.2°, and 21.3±0.2°.

In one embodiment, the present invention provides a crystalline Form I of compound (I) having a differential scanning calorimetry (DSC) thermogram pattern comprising an endothermic peak with a peak onset temperature of 55.3±1° C. and a peak maximum of 58.3±1° C.

In one embodiment, the present invention provides a crystalline Form II of compound (I) having an XRPD pattern exhibiting its six strongest characteristic peaks at the following 2θ reflection angles: 4.5±0.2°, 8.3±0.2°, 11.7±0.20, 16.6±0.2°, 18.2±0.2°, and 25.8±0.2°.

In one embodiment, the present invention provides a crystalline Form II of compound (I) having a DSC thermogram pattern comprising an endothermic peak with a peak onset temperature of 55.6±1° C. and a peak maximum of 61.8±1° C.

The present invention provides the crystalline Forms I and II of compound (I), which can remain stable when stored at room temperature without crystalline form transformation for commercial handling.

DETAILED DESCRIPTION OF THE INVENTION

Crystalline Form I of Compound (I) and Preparation Thereof

In an embodiment of the present invention, the method for preparing crystalline Form I of compound (I) comprises the steps of:

(I)

(a) dissolving crude compound (I) in a first solvent selected from the group consisting of ethyl ether, isopropyl ether, methyl tert-butyl ether, and mixtures thereof to form a homogenous solution;
(b) lowering the temperature and/or adding a second solvent selected from the group consisting of pentane, hexane, heptane, octane, nonane, decane, cyclopentane, cyclohexane, cycloheptane, and mixtures thereof to the homogeneous solution;
(c) stirring until a precipitate is formed;
(d) optionally adding the second solvent or a mixture of the first solvent and the second solvent for rinsing the precipitate;
(e) optionally filtering out the precipitate thereby isolating the crystalline Form I of compound (I); and
(f) optionally drying the crystalline Form I of compound (I).

The selection of the first solvent is an important factor to determine whether a crystalline Form I of compound (I) can be formed. The inventor found that it is very difficult to obtain a crystal of compound (I) using common solvents for commercial applications such as methyl isobutyl ketone, ethyl acetate, isopropyl acetate, toluene, xylene, acetone, dichloromethane, 1,4-dioxane, tetrahydrofuran, methanol, ethanol, propanol, butanol, benzyl alcohol, dimethyl sulfoxide, dimethylacetamide, dimethylformamide, and mixtures thereof as the first solvent. In the present invention, the first solvent used to dissolve the crude compound (I) is selected from the group consisting of ethyl ether, isopropyl ether, methyl tert-butyl ether, and mixtures thereof. In some embodiments, the volume of the first solvent may be about 0.5 ml to about 100 ml, preferably about 1 ml to about 50 ml, and more preferably about 2 ml to about 20 ml, per 1 g of the crude compound (I). When methyl tert-butyl ether is used as the first solvent, the volume is preferably less than about 20 ml, less than about 15 ml or less than about 10 ml. In some embodiments, the crude compound (I) can be dissolved in the first solvent at a temperature ranging from about 0° C. to about 60° C., preferably from about 10° C. to about 50° C., and more preferably from room temperature to about 40° C.

In one embodiment of the present invention, the temperature of the homogenous solution may be lowered to a temperature ranging from about −30° C. to about 50° C., preferably from about −20° C. to about 40° C., and more preferably from about −10° C. to about 30° C.

In a preferred embodiment, the volume of the second solvent selected from the group consisting of pentane, hexane, heptane, octane, nonane, decane, cyclopentane, cyclohexane, cycloheptane, and mixtures thereof may be about 0.1 ml to about 50 ml, preferably about 0.5 ml to about 20 ml, and more preferably about 2 ml to about 10 ml, per 1 ml of the first solvent. In some embodiments, the second solvent can be added at a temperature ranging from about −30° C. to about 50° C., preferably from about −20° C. to about 40° C., and more preferably from about −10° C. to about 30° C.

In one embodiment of the present invention, the precipitation of the crystal may be performed at a temperature ranging from about −30° C. to about 50° C., preferably from about −20° C. to about 40° C., and more preferably from about −10° C. to about 30° C.

In one embodiment of the present invention, the step of filtering out the precipitate comprises using the second solvent or a mixture of the first solvent and the second solvent to wash the precipitate. In the mixing of solvent, the ratio of the first solvent and the second solvent may be about 1:1 to about 1:100, preferably about 1:10 to about 1:50.

In one embodiment of the present invention, the crystalline Form I of compound (I) has an X-ray powder diffraction (XRPD) pattern exhibiting its six strongest characteristic peaks at the following 2θ reflection angles: 4.5±0.2°, 8.3±0.2°, 11.6±0.2°, 18.1±0.2°, 20.0±0.2°, and 21.3±0.2°. In a preferred embodiment, the XRPD pattern further comprises characteristic peaks at the following 2θ reflection angles: 9.7±0.20, 15.0±0.2°, 16.6±0.2°, 18.9±0.2°, 19.7±0.20, 20.3±0.2°, 22.2±0.2°, 23.4±0.2°, and 25.7±0.2°. More preferably, the XRPD pattern of the crystalline Form I of compound (I) is consistent with FIG. 1. The particular data of the crystalline Form I of compound (I) are shown in Table 1.

TABLE 1

Figure 1:
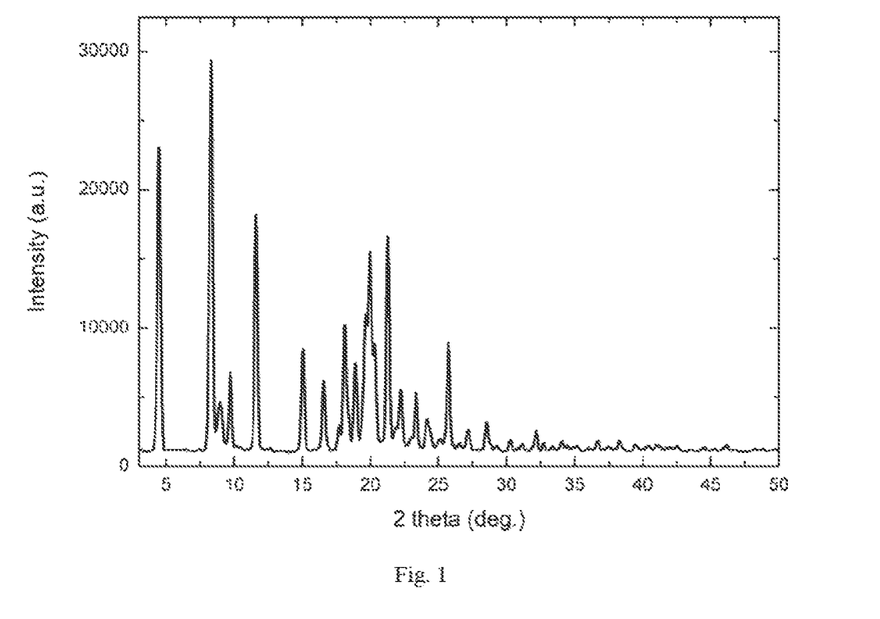
FIG. 1 shows an X-ray powder diffraction (XRPD) pattern of crystalline Form I of compound (I).

| 2θ angle (°) | d value (Å) | relative intensity (%) |
|---|---|---|
| 4.5 | 19.6 | 91.3 |
| 8.3 | 10.6 | 100.0 |
| 9.0 | 9.9 | 17.2 |
| 9.7 | 9.1 | 23.5 |
| 11.6 | 7.6 | 62.8 |
| 15.0 | 5.9 | 29.2 |
| 16.6 | 5.3 | 21.3 |
| 17.7 | 5.0 | 10.2 |
| 18.1 | 4.9 | 35.4 |
| 18.9 | 4.7 | 25.8 |
| 19.7 | 4.5 | 37.9 |
| 20.0 | 4.4 | 53.5 |
| 20.3 | 4.4 | 30.5 |
| 21.3 | 4.2 | 57.4 |
| 21.9 | 4.1 | 9.7 |
| 22.2 | 4.0 | 19.0 |
| 23.4 | 3.8 | 18.5 |
| 24.2 | 3.7 | 12.1 |

TABLE 1-continued

| 2θ angle (°) | d value (Å) | relative intensity (%) |
|---|---|---|
| 25.1 | 3.5 | 6.8 |
| 25.7 | 3.5 | 30.9 |
| 26.6 | 3.4 | 5.7 |
| 27.2 | 3.3 | 9.3 |
| 28.5 | 3.1 | 10.9 |
| 29.3 | 3.0 | 5.1 |
| 30.3 | 3.0 | 6.6 |
| 31.1 | 2.9 | 5.5 |
| 32.2 | 2.8 | 8.9 |
| 32.7 | 2.7 | 5.7 |
| 33.4 | 2.7 | 5.0 |
| 34.1 | 2.6 | 6.1 |
| 34.5 | 2.6 | 5.2 |
| 35.2 | 2.5 | 5.1 |
| 36.0 | 2.5 | 4.6 |
| 36.7 | 2.4 | 6.3 |
| 37.4 | 2.4 | 4.9 |
| 38.3 | 2.3 | 6.3 |
| 39.5 | 2.3 | 5.4 |
| 40.5 | 2.2 | 5.1 |
| 41.0 | 2.2 | 5.3 |
| 42.0 | 2.1 | 4.8 |
| 42.6 | 2.1 | 5.1 |
| 44.5 | 2.0 | 4.7 |
| 45.3 | 2.0 | 4.4 |
| 46.1 | 2.0 | 5.3 |
| 48.2 | 1.9 | 4.4 |
| 48.8 | 1.9 | 4.4 |

In one embodiment, the present invention provides a crystalline Form I of compound (I) having an XRPD pattern substantially as shown in FIG. 1.

Figure 2:
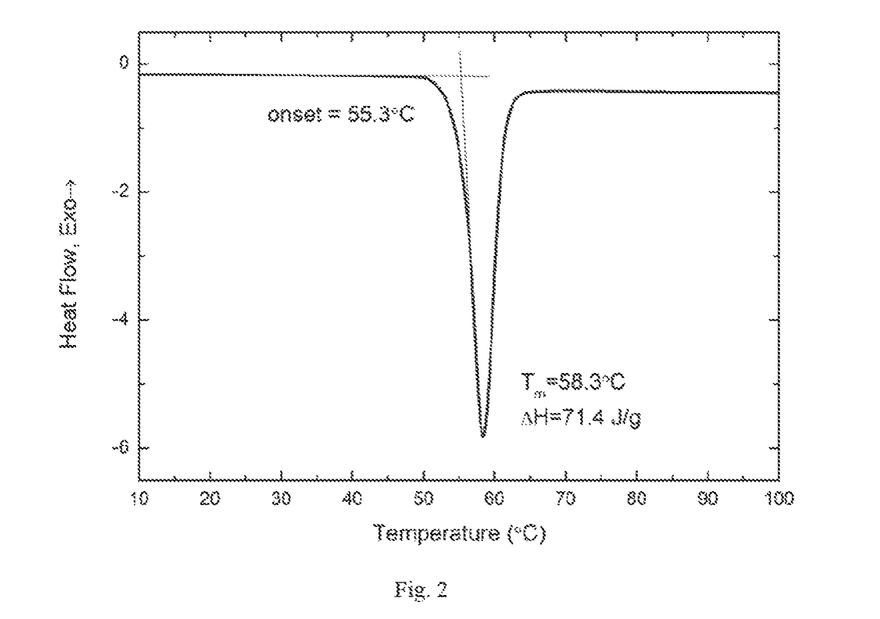
FIG. 2 shows a differential scanning calorimetry (DSC) thermogram pattern of crystalline Form I of compound (I).

In one embodiment, the present invention provides a crystalline Form I of compound (I) having a differential scanning calorimetry (DSC) thermogram pattern comprising an endothermic peak with a peak onset temperature of 55.3±1° C. and a peak maximum of 58.3±1° C. In a preferred embodiment, the present invention provides a crystalline Form I of compound (I) having a DSC thermogram pattern substantially as shown in FIG. 2.

Due to the use of the organic solvent system in the method of the present invention, the precipitated crystalline Form I of compound (I) possesses a compact solid characteristic and thus is easy to filter out. Moreover, the residual solvents can be easily removed under high vacuum at room temperature. The dried crystalline Form I of compound (I) with granular or powdery characteristic is much easier to weigh for commercial handling compared with the liquid form of compound (I) with high viscosity.

Figure 3:
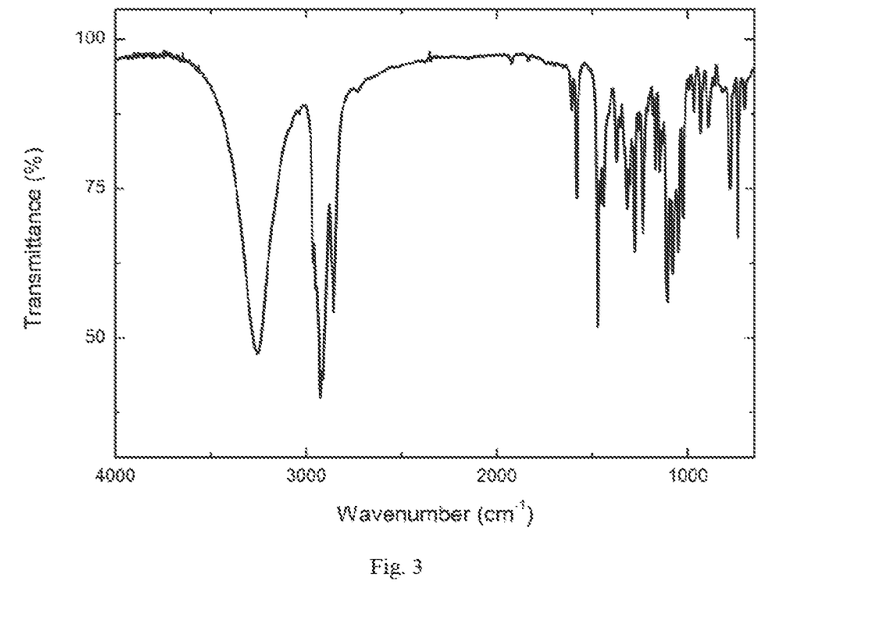
FIG. 3 shows a Fourier Transform Infrared (FTIR) spectrum of crystalline Form I of compound (I).

In one embodiment, the present invention provides a crystalline Form I of compound (I) having a 1% KBr Fourier Transform Infrared (FTIR) spectrum comprising peaks, in terms of cm$^{-1}$, at 3255±4 cm$^{-1}$, 3035±4 cm$^{-1}$, 2963±4 cm$^{-1}$, 2949±4 cm$^{-1}$, 2927±4 cm$^{-1}$, 2913±4 cm$^{-1}$, 2856±4 cm$^{-1}$, 1608±4 cm$^{-1}$, 1582±4 cm$^{-1}$, 1471±4 cm$^{-1}$, 1456±4 cm$^{-1}$, 1440±4 cm$^{-1}$, 1373±4 cm$^{-1}$, 1354±4 cm$^{-1}$, 1317±4 cm$^{-1}$, 1304±4 cm$^{-1}$, 1289±4 cm$^{-1}$, 1277±4 cm$^{-1}$, 1257±4 cm$^{-1}$, 1236±4 cm$^{-1}$, 1210±4 cm$^{-1}$, 1184±4 cm$^{-1}$, 1169±4 cm$^{-1}$, 1148±4 cm$^{-1}$, 1134±4 cm$^{-1}$, 1106±4 cm$^{-1}$, 1092±4 cm$^{-1}$, 1080±4 cm$^{-1}$, 1049±4 cm$^{-1}$, 1027±4 cm$^{-1}$, 968±4 cm$^{-1}$, 933±4 cm$^{-1}$, 891±4 cm$^{-1}$, 779±4 cm$^{-1}$, 775±4 cm$^{-1}$, 737±4 cm$^{-1}$, and 702±4 cm$^{-1}$. In a preferred embodiment, the present invention provides a crystalline Form I of compound (I) having a 1% KBr FTIR spectrum substantially as shown in FIG. 3.

The FTIR result comprising peaks, in terms of cm$^{-1}$, at 3359 cm$^{-1}$, 2931 cm$^{-1}$, 2860 cm$^{-1}$, 2249 cm$^{-1}$, 929 cm$^{-1}$, and 745 cm$^{-1}$ for compound (I) as a viscous liquid is disclosed by *J. Org. Chem.*, 2004, 69, 1890-1902, which is obviously different from the FTIR features of the crystalline Form I of compound (I).

Crystalline Form II of Compound (I) and Preparation Thereof

In an embodiment of the present invention, the method for preparing crystalline Form II of compound (I) comprises the steps of:

(I)

(a) dissolving crude compound (I) in a third solvent of methyl tert-butyl ether to form a homogenous solution;
(b) lowering the temperature and/or adding a fourth solvent selected from the group consisting of pentane, hexane, heptane, octane, nonane, decane, cyclopentane, cyclohexane, cycloheptane, and mixtures thereof to the homogeneous solution;
(c) stirring until a precipitate is formed;
(d) optionally adding the fourth solvent or a mixture of the third solvent and the fourth solvent for rinsing the precipitate;
(e) optionally filtering out the precipitate thereby isolating the crystalline Form II of compound (I); and
(f) optionally drying the crystalline Form II of compound (I).

In the present invention, the third solvent used to dissolve the crude compound (I) is methyl tert-butyl ether. A crystalline Form II of compound (I) cannot be obtained using other solvents such as ethyl ether and isopropyl ether as the third solvent. In some embodiments, the volume of the third solvent is an important factor to determine whether a crystal Form II of compound (I) can be formed. In some embodiments, the volume of the third solvent may be about 20 ml or more, about 20 ml to about 200 ml, about 25 ml to about 100 ml, or about 30 ml to about 50 ml, per 1 g of the crude compound (I). In some embodiments, the crude compound (I) can be dissolved in the third solvent at a temperature ranging from about 0° C. to about 60° C., preferably from about 10° C. to about 50° C., and more preferably from room temperature to about 40° C.

In one embodiment of the present invention, the temperature of the homogenous solution may be lowered to a temperature ranging from about −30° C. to about 50° C., preferably from about −20° C. to about 40° C., and more preferably from about −10° C. to about 30° C.

In a preferred embodiment, the volume of the fourth solvent selected from the group consisting of pentane, hexane, heptane, octane, nonane, decane, cyclopentane, cyclohexane, cycloheptane, and mixtures thereof may be about 10 ml to about 200 ml, preferably about 20 ml to about 150 ml, and more preferably about 30 ml to about 100 ml, per 1 ml of the third solvent. In some embodiments, the fourth solvent can be added at a temperature ranging from about −30° C. to about 50° C., preferably from about −20° C. to about 40° C., and more preferably from about −10° C. to about 30° C.

In one embodiment of the present invention, the precipitation of the crystal may be performed at a temperature ranging from about −30° C. to about 50° C., preferably from about −20° C. to about 40° C., and more preferably from about −10° C. to about 30° C.

In one embodiment of the present invention, the step of filtering out the precipitate comprises using the fourth solvent or a mixture of the third solvent and the fourth solvent to wash the precipitate. In the mixing of solvent, the ratio of the third solvent and the fourth solvent may be about 1:1 to about 1:100, preferably about 1:10 to about 1:50.

In one embodiment of the present invention, the crystalline Form II of compound (I) has an XRPD pattern exhibiting its six strongest characteristic peaks at the following 2θ reflection angles: 4.5±0.2°, 8.3±0.2°, 11.7±0.20, 16.6±0.2°, 18.2±0.2°, and 25.8±0.2°. In a preferred embodiment, the XRPD pattern further comprises characteristic peaks at the following 2θ reflection angles: 9.0±0.2°, 9.8±0.2°, 15.1±0.2°, 17.7±0.20, 19.0±0.2°, 20.1±0.20, 20.4±0.2°, 21.4±0.2°, and 22.2±0.2°. More preferably, the XRPD pattern of the crystalline Form II of compound (I) is consistent with FIG. 4. The particular data of the crystalline Form II of compound (I) are shown in Table 2.

TABLE 2

Figure 4:
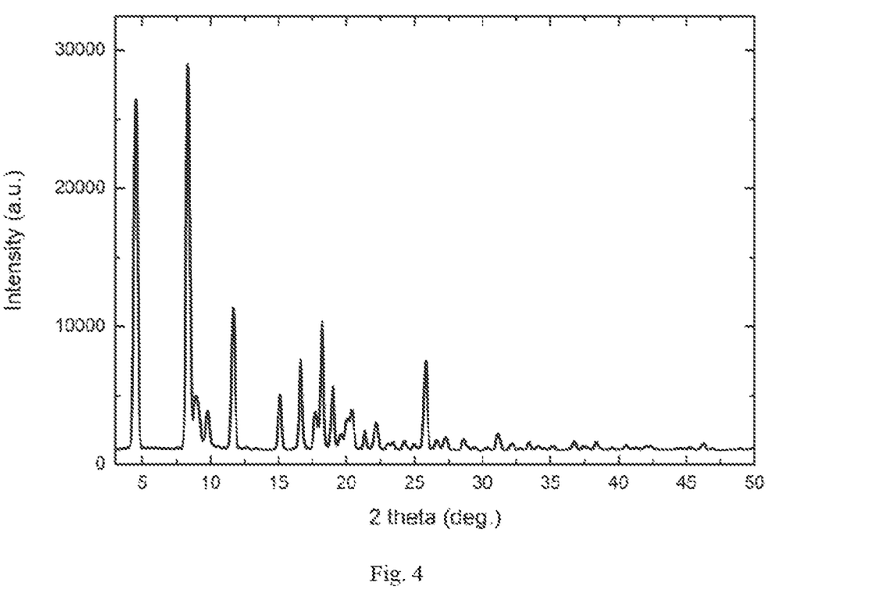
FIG. 4 shows an X-ray powder diffraction (XRPD) pattern of crystalline Form II of compound (I).

| 2 angle (°) | d value (Å) | relative intensity (%) |
|---|---|---|
| 4.5 | 19.6 | 91.3 |
| 8.3 | 10.6 | 100.0 |
| 9.0 | 9.9 | 17.2 |
| 9.8 | 9.0 | 13.3 |
| 11.7 | 7.6 | 39.3 |
| 15.1 | 5.9 | 17.8 |
| 16.6 | 5.3 | 26.2 |
| 17.7 | 5.0 | 13.1 |
| 18.2 | 4.9 | 35.8 |
| 19.0 | 4.7 | 19.6 |
| 19.6 | 4.5 | 7.6 |
| 20.1 | 4.4 | 11.5 |
| 20.4 | 4.4 | 13.7 |
| 21.4 | 4.2 | 8.5 |
| 22.2 | 4.0 | 10.6 |
| 23.1 | 3.9 | 5.1 |
| 23.4 | 3.8 | 5.5 |
| 24.2 | 3.7 | 5.7 |
| 25.0 | 3.6 | 5.1 |
| 25.8 | 3.4 | 25.9 |
| 26.6 | 3.3 | 6.1 |
| 27.3 | 3.3 | 6.8 |
| 28.6 | 3.1 | 6.4 |
| 29.4 | 3.0 | 4.3 |
| 30.3 | 2.9 | 4.3 |
| 31.1 | 2.9 | 7.7 |
| 32.2 | 2.8 | 5.2 |
| 32.8 | 2.7 | 4.0 |
| 33.4 | 2.7 | 5.5 |
| 34.1 | 2.6 | 4.6 |
| 35.1 | 2.6 | 4.5 |
| 36.7 | 2.4 | 5.6 |
| 37.4 | 2.4 | 4.6 |
| 38.4 | 2.3 | 5.5 |
| 39.5 | 2.3 | 4.3 |
| 40.5 | 2.2 | 4.8 |
| 41.4 | 2.2 | 4.3 |
| 42.4 | 2.1 | 4.6 |
| 44.5 | 2.0 | 4.1 |
| 45.3 | 2.0 | 4.4 |
| 46.2 | 2.0 | 5.2 |
| 46.9 | 1.9 | 4.0 |
| 48.9 | 1.9 | 4.1 |

In one embodiment, the present invention provides a crystalline Form II of compound (I) having an XRPD pattern substantially as shown in FIG. 4.

Figure 5:
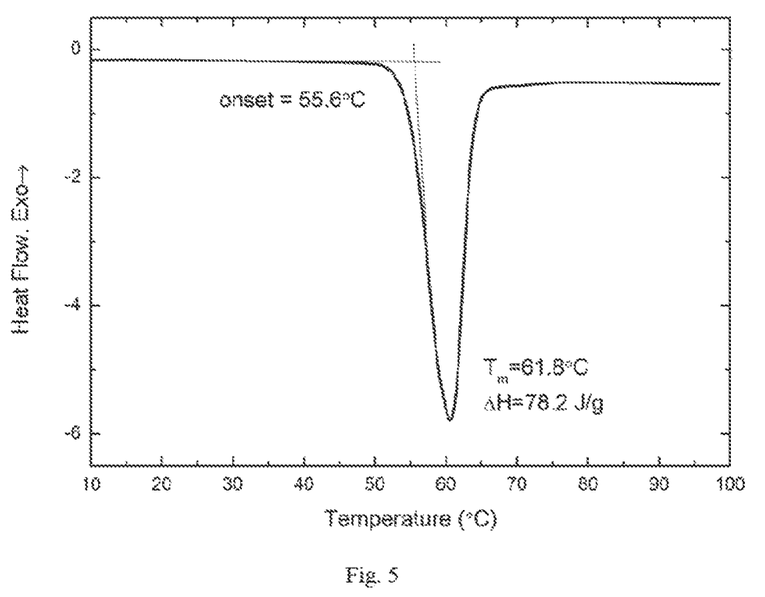
FIG. 5 shows a differential scanning calorimetry (DSC) thermogram pattern of crystalline Form II of compound (I).

In one embodiment, the present invention provides a crystalline Form II of compound (I) having a DSC thermogram pattern comprising an endothermic peak with a peak onset temperature of 55.6±1° C. and a peak maximum of 61.8±1° C. In a preferred embodiment, the present invention provides a crystalline Form II of compound (I) having a DSC thermogram pattern substantially as shown in FIG. 5.

Due to the use of the organic solvent system in the method of the present invention, the precipitated crystalline Form II of compound (I) possesses a compact solid characteristic and thus is easy to filter out. Moreover, the residual solvents can be easily removed under high vacuum at room temperature. The dried crystalline Form II of compound (I) with granular or powdery characteristic is much easier to weight for commercial handling compared with the liquid form of compound (I) with high viscosity.

Figure 6:
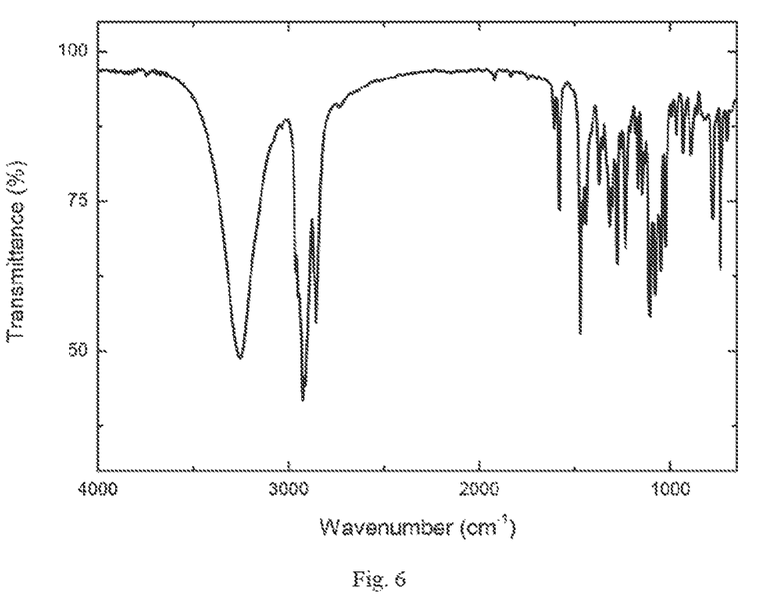
FIG. 6 shows a Fourier Transform Infrared (FTIR) spectrum of crystalline Form II of compound (I).

In one embodiment, the present invention provides a crystalline Form II of compound (I) having a 1% KBr FTIR spectrum comprising peaks, in terms of $cm^{-1}$, at 3255±4 $cm^{-1}$, 3035±4 $cm^{-1}$, 2963±4 $cm^{-1}$, 2949±4 $cm^{-1}$, 2927±4 $cm^{-1}$, 2913±4 $cm^{-1}$, 2856±4 $cm^{-1}$, 1608±4 $cm^{-1}$, 1582±4 $cm^{-1}$, 1471±4 $cm^{-1}$, 1456±4 $cm^{-1}$, 1440±4 $cm^{-1}$, 1373±4 $cm^{-1}$, 1354±4 $cm^{-1}$, 1317±4 $cm^{-1}$, 1304±4 $cm^{-1}$, 1289±4 $cm^{-1}$, 1277±4 $cm^{-1}$, 1257±4 $cm^{-1}$, 1236±4 $cm^{-1}$, 1210±4 $cm^{-1}$, 1184±4 $cm^{-1}$, 1169±4 $cm^{-1}$, 1148±4 $cm^{-1}$, 1134±4 $cm^{-1}$, 1106±4 $cm^{-1}$, 1092±4 $cm^{-1}$, 1080±4 $cm^{-1}$, 1049±4 $cm^{-1}$, 1027±4 $cm^{-1}$, 968±4 $cm^{-1}$, 933±4 $cm^{-1}$, 891±4 $cm^{-1}$, 779±4 $cm^{-1}$, 775±4 $cm^{-1}$, 737±4 $cm^{-1}$, and 702±4 $cm^{-1}$. In a preferred embodiment, the present invention provides a crystalline Form II of compound (I) having a 1% KBr FTIR spectrum substantially as shown in FIG. 6.

The FTIR result comprising peaks, in terms of $cm^{-1}$, at 3359 $cm^{-1}$, 2931 $cm^{-1}$, 2860 $cm^{-1}$, 2249 $cm^{-1}$, 929 $cm^{-1}$, and 745 $cm^{-1}$ for compound (I) as a viscous liquid is disclosed by J. Org. Chem., 69, 1890-1902, which is obviously different from the FTIR features of the crystalline Form II of compound (I).

According to the present disclosure, the six strongest characteristic peaks of the XRPD pattern for crystalline Form I of compound (I) are located at the following 2θ reflection angles: 4.5±0.2°, 8.3±0.2°, 11.7±0.20, 16.6±0.2°, 18.2±0.2°, and 25.8±0.2°, and the six strongest characteristic peaks of the XRPD pattern for crystalline Form II of compound (I) are located at the following 2θ reflection angles: 4.5±0.2°, 8.3±0.2°, 11.6±0.2°, 18.1±0.2°, 20.0±0.2°, and 21.3±0.2°. Although the positions of characteristic peaks of XRPD pattern for crystalline Form I of compound (I) are similar compared with those for crystalline Form II of compound (I), the relative intensity of characteristic peaks for crystalline Form I and Form II of compound (I) are obviously different from each other. Moreover, the relative intensity of characteristic peaks of XRPD pattern shows a difference at around 15 to 250 (d value about 6.5-3 Å belongs to the distance of intra-molecule ordering) for crystalline Form I and Form II of compound (I), indicating that the intra-molecule arrangement of crystalline Form I and Form II of compound (I) are different, as shown in FIG. 1 and FIG. 4. On the other hand, the melting points (peak maximum) of the DSC thermogram pattern are 58.3±1° C. for crystalline Form I of compound (I) and 61.8±1° C. for crystalline Form II of compound (I), indicating that crystal structures of crystalline Form I and Form II of compound (I) are different. According to above discussion, the inventor identified that the crystalline Form I and Form II of compound (I) are two different crystalline forms.

In addition, the Form I and Form II crystals of compound (I) are both stable crystalline forms, which show good stability, with no other crystalline forms or degraded products of impurities at room temperature for six months. Moreover, the assay of compound (I) Form I and Form II crystal can be kept between 98.0% and 102.0% even after six months of placement under normal storage temperature (5° C. and −20° C.). However, the Form II crystal of compound (I) will convert to Form I crystal by simply grinding it at room temperature for about 10 minutes.

It will be understood that particular embodiments described herein are shown by way of illustration and not as limitations of the invention. The principal features of this invention can be employed in various embodiments without departing from the scope of the invention. Those skilled in the art will recognize or be able to ascertain, using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

All of the compounds and/or methods disclosed and claimed herein can be made and executed without undue experimentation in light of the present disclosure. While the compounds and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

EXAMPLES

X-ray Powder Diffraction (XRPD) Analysis: The XRPD patterns were collected on a Bruker D2 PHASER diffractometer with fixed divergence slits and 1D LYNXEYE detector. The samples (ca. 100 mg) were flatly placed on a sample holder. The prepared samples were analyzed over a 2θ range from 2° to 500 with step size of 0.02 degrees and step time of 1 second using $CuK_\alpha$ radiation at a power of 10 mA and 30 kV. The $CuK_\beta$ radiation was removed by a divergent beam nickel filter.

Differential Scanning Calorimetry (DSC) Analysis: The DSC thermogram patterns were collected on a TA DISCOVERY DSC25 instrument. The samples (ca. 5 mg) were weighed into an aluminum pan with a crimping closed aluminum lid. The prepared samples were analyzed from 10° C. to 100° C. at scan rate of 10° C./min under a flow of nitrogen (ca. 50 ml/min). The melting temperature and heat of fusion were calibrated by indium (In) before measurement.

Fourier Transform Infrared (FTIR) Analysis: The FTIR spectra were collected on a Perkin Elmer SPECTRUM 100 instrument. The samples were mixed with potassium bromide (KBr) in an approximately 1:100 ratio (w/w) using an agate mortar and pestle. The mixture was compressed in a pellet die at a pressure of about 10 to 13 tonnes for 2 minutes. The resulting disk was scanned 4 times versus a collected background from 4000 $cm^{-1}$ to 650 $cm^{-1}$ at a resolution of 4 $cm^{-1}$. The data was baseline corrected and normalized.

Example 1

Preparation of Crude Compound (I)

(1R,2R,3aS,9aS)-1-((S)-3-hydroxyoctyl)-2,3,3a,4,9,9a-hexahydro-1H-cyclopenta[b]naphthalene-2,5-diol (20.00 g, 0.06 mol) in dry acetone (200 ml) was treated with potassium carbonate (20.70 g, 0.15 mol), chloroacetonitrile (6.40 ml, 0.10 mol) and tetrabutylbromide (3.20 g, 0.01 mmol). The mixture was heated at 30° C. overnight. Then, the reaction mixture was filtered with celite pad. The filtrate was evaporated off under vacuum. The crude product was purified by chromatography on silica gel using a mixture of hexane and ethyl acetate as a gradient eluent to obtain 16.4 g viscous liquid (crude compound (I)).

Example 2

Preparation of Crystalline Form I of Compound (I)

Crude compound (I) (1.00 g, from Example 1) and isopropyl ether (15 ml) were heated to 40° C. for dissolution and then cooled to room temperature. N-heptane (17 ml) was added slowly dropwise and the mixture was stirred in ice water bath for 20 hours until solid precipitation occurred. Afterwards, the resulting suspension was filtered and rinsed, and then dried under high vacuum at room temperature for 24 hours to give 0.90 g crystalline Form I of compound (I). The XRPD, DSC, and FTIR results are the same as shown in FIG. 1, FIG. 2, and FIG. 3.

Example 3

Preparation of Crystalline Form I of Compound (I)

Crude compound (I) (1.01 g, from Example 1) and ethyl ether (10 ml) were heated to 40° C. for dissolution and then cooled to room temperature. N-pentane (11 ml) was added slowly dropwise and the mixture was stirred in ice water bath for 24 hours until solid precipitation occurred. Afterwards, the resulting suspension was filtered and rinsed, and then dried under high vacuum at room temperature for 24 hours to give 0.91 g crystalline Form I of compound (I). The XRPD, DSC, and FTIR results are the same as shown in FIG. 1, FIG. 2, and FIG. 3.

Example 4

Preparation of Crystalline Form I of Compound (I)

Crude compound (I) (1.00 g, from Example 1) and methyl tert-butyl ether (10 ml) were heated to 40° C. for dissolution and then cooled to room temperature. N-hexane (10 ml) was added slowly dropwise and the mixture was stirred in ice water bath for 24 hours until solid precipitation occurred. Afterwards, the resulting suspension was filtered and rinsed, and then dried under high vacuum at room temperature for 24 hours to give 0.90 g crystalline Form I of compound (I). The XRPD, DSC, and FTIR results are the same as shown in FIG. 1, FIG. 2, and FIG. 3.

Example 5

Preparation of Crystalline Form II of Compound (I)

Crude compound (I) (1.00 g, from Example 1) and methyl tert-butyl ether (20 ml) were heated to 40° C. for dissolution and then cooled to room temperature. N-hexane (25 ml) was added slowly dropwise and the mixture was stirred in ice water bath for 24 hours until solid precipitation occurred. Afterwards, the resulting suspension was filtered and rinsed, and then dried under high vacuum at room temperature for 24 hours to give 0.53 g crystalline Form II of compound (I). The XRPD, DSC, and FTIR results are the same as shown in FIG. 4, FIG. 5, and FIG. 6.

Example 6

Preparation of Crystalline Form II of Compound (I)

Crude compound (I) (1.00 g, from Example 1) and methyl tert-butyl ether (30 ml) were heated to 40° C. for dissolution and then cooled to room temperature. N-heptane (40 ml) was added slowly dropwise and the mixture was stirred in ice water bath for 24 hours until solid precipitation occurred. Afterwards, the resulting suspension was filtered and rinsed, and then dried under high vacuum at room temperature for 24 hours to give 0.51 g crystalline Form II of compound (I). The XRPD, DSC, and FTIR results are the same as shown in FIG. 4, FIG. 5, and FIG. 6.

What is claimed is:

1. A crystalline Form I of compound (I), characterized by having an X-ray powder diffraction (XRPD) pattern comprising its six strongest characteristic peaks at the following 2θ reflection angles: 4.5±0.2°, 8.3±0.2°, 11.6±0.2°, 18.1±0.2°, 20.0±0.2°, and 21.3±0.2°

(I)

2. The crystalline Form I of compound (I) of claim 1, wherein the XRPD pattern further comprises characteristic peaks at the following 2θ reflection angles: 9.7±0.2°, 15.0±0.2°, 16.6±0.2°, 18.9±0.2°, 19.7±0.2°, 20.3±0.2°, 22.2±0.2°, 23.4±0.2°, and 25.7±0.2°.

3. The crystalline Form I of compound (I) of claim 1, wherein the XRPD pattern is substantially shown in FIG. 1.

4. The crystalline Form I of compound (I) of claim 1, further having a differential scanning calorimetry (DSC) thermogram pattern comprising an endothermic peak with a peak onset temperature of approximately 55.3±1° C. and a peak maximum of approximately 58.3±1° C.

5. The crystalline Form I of compound (I) of claim 4, wherein the DSC thermogram pattern is substantially shown in FIG. 2.

6. A method for preparing the crystalline Form I of compound (I) according to claim 2, which comprises the steps of:
dissolving compound (I) in a first solvent selected from the group consisting of ethyl ether, isopropyl ether, methyl tert-butyl ether, and mixtures thereof to form a homogenous solution;
lowering the temperature and/or adding a second solvent selected from the group consisting of pentane, hexane, heptane, octane, nonane, decane, cyclopentane, cyclohexane, cycloheptane, and mixtures thereof to the homogenous solution; and
stirring until a precipitate is formed;
provided that when methyl tert-butyl ether is used as the first solvent, the volume of the first solvent is less than about 20 ml per 1 g of the crude compound (I).

7. The method of claim 6, further comprising the steps of:
adding the second solvent or a mixture of the first solvent and the second solvent for rinsing the precipitate;
filtering out the precipitate, thereby isolating the crystalline Form I of compound (I); and
optionally drying the crystalline Form I of compound (I).

8. A crystalline Form II of compound (I), characterized by having an XRPD pattern comprising its six strongest characteristic peaks at the following 2θ reflection angles: 4.5±0.2°, 8.3±0.2°, 11.7±0.2°, 16.6±0.2°, 18.2±0.20, and 25.8±0.2°.

9. The crystalline Form II of compound (I) of claim 8, wherein the XRPD pattern further comprises characteristic peaks at the following 2θ reflection angles: 9.0±0.2°, 9.8±0.2°, 15.1±0.2°, 17.7±0.2°, 19.0±0.2°, 20.1-0.2°, 20.4±0.2°, 21.4±0.2°, and 22.2±0.2°

(I)

10. The crystalline Form II of compound (I) of claim 8, wherein the XRPD pattern is substantially shown in FIG. 4.

11. The crystalline Form II of compound (I) of claim 8, further having a DSC thermogram pattern comprising an endothermic peak with a peak onset temperature of approximately 55.6±1° C. and a peak maximum of approximately 61.8±1° C.

12. The crystalline Form II of compound (I) of claim 11, wherein the DSC thermogram pattern is substantially shown in FIG. 5.

13. A method for preparing the crystalline Form II of compound (I) according to claim 9, which comprises the steps of:
- dissolving compound (I) in a third solvent of methyl tert-butyl ether to form a homogenous solution, the volume of the third solvent being about 20 ml or more per 1 g of the compound (I);
- lowering the temperature and/or adding a fourth solvent selected from the group consisting of pentane, hexane, heptane, octane, nonane, decane, cyclopentane, cyclohexane, cycloheptane, and mixtures thereof to the homogenous solution; and
- stirring until a precipitate is formed.

14. The method of claim 13, further comprising the steps of:
- adding the fourth solvent or a mixture of the third solvent and the fourth solvent for rinsing the precipitate;
- filtering out the precipitate, thereby isolating the crystalline Form II of compound (I); and
- optionally drying the crystalline Form II of compound (I).

* * * * *